US009330295B2

(12) United States Patent
Dunn

(10) Patent No.: US 9,330,295 B2
(45) Date of Patent: May 3, 2016

(54) SPATIAL SEQUENCING/GENE EXPRESSION CAMERA

(71) Applicant: BROWN UNIVERSITY, Providence, RI (US)

(72) Inventor: Casey Dunn, Providence, RI (US)

(73) Assignee: BROWN UNIVERSITY, Providence, RI (US)

(*) Notice: Subject to any disclaimer, the term of this patent is extended or adjusted under 35 U.S.C. 154(b) by 26 days.

(21) Appl. No.: 14/215,748

(22) Filed: Mar. 17, 2014

(65) Prior Publication Data

US 2014/0270435 A1    Sep. 18, 2014

Related U.S. Application Data

(60) Provisional application No. 61/791,531, filed on Mar. 15, 2013.

(51) Int. Cl.
| | |
|---|---|
| *G06K 9/00* | (2006.01) |
| *G06F 19/26* | (2011.01) |
| *C12Q 1/68* | (2006.01) |
| *G06F 19/22* | (2011.01) |

(52) U.S. Cl.
CPC ............ *G06K 9/00127* (2013.01); *G06F 19/26* (2013.01); *G06F 19/22* (2013.01)

(58) Field of Classification Search
CPC ............. G06K 9/00; G06F 19/00; G06T 7/00
USPC ............. 382/128–134; 424/1.69, 1.11, 138.1; 435/6.11, 6.13, 188, 330, 375, 376
See application file for complete search history.

(56) References Cited

U.S. PATENT DOCUMENTS

| 7,833,701 B2 * | 11/2010 | Oshima ................ B01J 19/0046 435/458 |
| 2009/0081688 A1 * | 3/2009 | Luo ...................... C12Q 1/6841 435/6.16 |

OTHER PUBLICATIONS

Lee et al. "Highly Multiplexed Subcellular RNA Sequencing in Situ" 2014, Science 343: 1360-1363.

*Primary Examiner* — Abolfazl Tabatabai
(74) *Attorney, Agent, or Firm* — Lawson & Weitzen LLP; Sonia K. Guterman; Michael I. Falkoff

(57) ABSTRACT

Methods, articles and systems that provide imagewise mapping or display of gene expression of a biosample, by contacting the biosample, such as a tissue slice or metacommunity, to a detector which captures material from the biosample and processes the captured material. In one embodiment the detector has an array of one or more capture sites at defined positions on the detector, each site carrying an immobilized capture oligonucleotide and a site-indexing oligonucleotide. The array captures mRNA from the biosample contacted thereto, and the captured mRNA is processed to form a sequenceable amount of amplified captured material which includes the site-indexing oligonucleotide, so that when sequenced, detection of the site-indexing oligonucleotide indicates the original capture location on the array, thereby mapping the sequenced material to its capture location and imaging display of gene expression distribution in the original biosample. In some embodiments the site-encoding sequence is integrated with the capture oligonucleotide. In other embodiments, the detector is a modified sequencing flow cell, which is opened to allow the biospecimen to be contacted to a capture surface; processing is performed while the material remains on the capture surface and locations of the resulting sequences correspond to the location of origin of the templates of the biomolecules in the sample. The spatially resolved sequencing, gene expression camera and technology in various embodiments are applied to genome sequences and DNA fragments present in the biosample, for example to study or diagnose developmental, disease, and tumor conditions.

9 Claims, 3 Drawing Sheets

SPATIAL SEQUENCING/GENE EXPRESSION CAMERA

RELATED APPLICATION

This application is related to and claims the benefit of U.S. provisional application Ser. No. 61/791,531 filed Mar. 15, 2013 entitled, "Spatial sequencing/gene expression camera". The full text, including drawings and appendices of the provisional application are hereby incorporated herein by reference in its entirety.

BACKGROUND

The present invention relates to methods and apparatus for analyzing the spatial distribution of gene expression. Gene expression, the transcription of genetic information from DNA in the nucleus into messenger RNA (mRNA) for translation into a protein, is one of the most critical aspects of gene activity. At present, most gene expression studies can investigate only a small number of genes at high spatial resolution (for example, by in situ mRNA hybridization in tissues using probes to specific genes), or investigate a large number of genes at very poor spatial resolution (for example, using a microarray or next-generation nucleotide sequencing of RNA from a small number of dissected tissue regions).

Many commercial applications and scientific questions of broad interest require expression data for a large number of genes over a spatially resolved region, with a high number of sequences. Such spatial analyses could for example, consider the spatial distribution of gene expression in a tissue formed of multiple cell types, expression in contiguous diseased and non-diseased cells, expression in a tumor mass or neighboring tissues, or across a tissue boundary.

SUMMARY

The invention in various embodiments and associated methods of use described here improve the ease and spatial resolution of sequencing-based approaches to determine the spatial distribution, or pattern of distribution, of DNA or RNA molecules in a biospecimen. The term "biospecimen' as used herein refers to a tissue sample obtained from an organism. The tissue sample includes biopsy samples, autopsy samples, excised tissue and tumor samples including archived specimens and both fresh and preserved specimens. To determine the spatial distribution of biomolecules a detector captures the biomolecules from a specimen according to the methods herein, which preserve information about the location of the biomolecules. The simultaneous determinations are made using data and signal processing to obtain both the location and the nucleotide sequence of genetic or genetically determined material, primarily RNA or DNA molecules or both in a biospecimen. The methods herein eliminate the steps used previously to prepare pools of RNA or DNA from particular tissue regions or specifically identified tissue sub-regions. The location is a histological point within a cell or anatomic point within a tissue. Subsequent sequencing of a large number of biomolecules is then performed external to the tissue.

In an embodiment of a device and a system referred to herein as a gene expression camera or gene expression imaging system, the invention involves direct application of DNA or RNA from a biospecimen, which may be a tissue slice, onto sites of the detector by contacting the biospecimen to the detector. The detector functions as a spatially-resolving capture element that captures material from the biospecimen such that the spatial distribution of the DNA or RNA molecules within the tissue is preserved on the two dimensional capture surface or substrate having the capture array. The captured material is then processed to obtain both nucleotide sequence and position information. In various embodiments of the methods and systems herein, the captured material is sequenced on the capture surface, and the sequence data is overlaid on a tissue image to map sequenced material to tissue sites or points of origin. In further embodiments, the captured biomolecule is modified after capture by adding a position-encoding subsequence that is address specific, thereby encoding the capture position alternatively, the detector contains address specific sequence information. The modified biomolecule, which is a polynucleotide, is then amplified and sequenced, and the capture position recovered from the sequencing operation to map back onto the tissue site of origin, providing a spatially resolved image of gene expression. The term "spatially resolved image" as used herein refers to an image of a biospecimen or biological material in which the lines of pixels per unit length are closely resolved. Spatial resolution depends on properties of the system creating the image including the pixel resolution in pixels per inch. The clarity of the image is a function of density such that spatial resolution is a function of total number of pixels in an area of an image. Spatial resolution is the number of independent pixel values per unit length. The term "spatial array" as used herein refers to capture surfaces arranged in spatially separated points, each point containing a specific capture biomolecule.

Samples of a biospecimen in an embodiment of the method herein are prepared for expression imaging by cryoslicing, which exposes mRNA and maintains physical integrity of cellular and tissue structures in the frozen material. When the mRNA is initially immobilized on the detector by directly contacting a tissue slice to the detector, the mRNA from a point in the slice is captured at a corresponding location on the detector. By first forming a microscope image of a slice (or adjacent slices), and then placing the slice on the detector, the spatially-resolved gene expression data are isometrically mapped to the tissue image, and integrated with anatomical data or features represented in the corresponding image locations.

The detector may be embodied as a sample preparation device upon which the sample tissue is placed, and which produces a spatially encoded DNA library ready for sequencing on another instrument, such that each molecule in the library includes a location-specific subsequence that is incorporated alongside the sequence captured from the sample to indicate its position of origin on the detector array (hence contacted position of the specimen itself). Alternatively, the invention is realized as a modified sequencing instrument. In this case, the detector is a modified sequencing flow cell having a capture element or capture surface in a flow assembly. The term "sequencing flow cell" as used herein refers to a method in which the sample of nucleic acid to be sequenced is removed to the array from the specimen hybridized in situ and the nucleic acid is sequenced on the array surface.

The assembly is opened to contact the specimen to the capture surface/flow cell, the biomolecules are captured and anchored on the flow cell, and the biomolecules are prepared for nucleotide sequencing while attached to the same surface. In this case, the actual physical location of each sequencing molecule on the capture element, rather than the inclusion of a location-specific coded DNA subsequence, gives the spatial location data for the physical location of origin of the sequence in the sample.

As a sample preparation device, the detector of the gene expression camera is an oligonucleotide array having sites (herein denoted pixels) each of which is a point or small region having a defined positional location (address molecule) on the detector. The detector may be formed, for example, as a treated slide, such as a microscope slide, which constitutes a prepared array, such as a microarray, having a desired spatial pattern and extent. Each pixel of the array has a mix of generic DNA anchors for capturing mRNA from the tissue, and barcoded DNA molecules that have a sequence unique to the pixel, i.e., that encode the pixel location on the detector. In some embodiments, the capture sequence and barcode may be incorporated into a single pixel-specific polynucleotide molecule. The mRNA of the specimen is captured by hybridization after contacting the specimen to the detector, and once the mRNA is immobilized on the anchors and the tissue debris is washed away, the anchors are used to prime complimentary DNA (cDNA) synthesis. The barcode sequence is integrated during cDNA synthesis, either as part of the priming adapter (if the barcode is integrated with the capture molecule) or by template switching or other mechanism (if the capture and barcode sequences have been co-deposited as separate molecules at each pixel of the detector array). The resulting position-encoded cDNA is then cleaved from the camera, and is processed and sequenced on any modern high-throughput nucleotide sequencer, such as an Illumina HiSeq, Life Technology Proton Torrent, or Roche 454. The resulting nucleotide sequence data encodes gene identity (the portion of the cDNA derived by reverse transcription from mRNA) and location (indicated by the portion of the cDNA derived from the pixel-specific barcode), and is computationally converted back into two-dimensional images spanning the region and mapping the expression of all genes expressed in the tissue or other biosample that was initially contacted to the array.

In the sequencing flow cell embodiment the detector is modified so that it is physically opened to remove the sample and apply the sample to the capture surface viz., detector surface or flow cell, such that the nucleic acids and the polynucleotide-related biomolecules from the sample are captured directly onto the surface of the detector. All steps of preparation of those molecules for sequencing can then occur while the captured material remains immobilized on the detector surface. Rather than be labeled with a location-specific barcode subsequence for detection during subsequent sequencing, the sample is prepared for sequencing and sequenced without ever being released from the detector surface. The location of the sequencing reaction on the surface of the detector therefore corresponds to the location of the original molecule in the biosample, and the distribution of sequences may be overlaid on an image of the sample to correlate the displayed sequences and the visible anatomical or structural features of the original biosample.

BRIEF DESCRIPTION OF THE DRAWINGS

Features of the invention will be understood from the description provided herein, together with the Figures, wherein.

DETAILED DESCRIPTION

Figure 1:
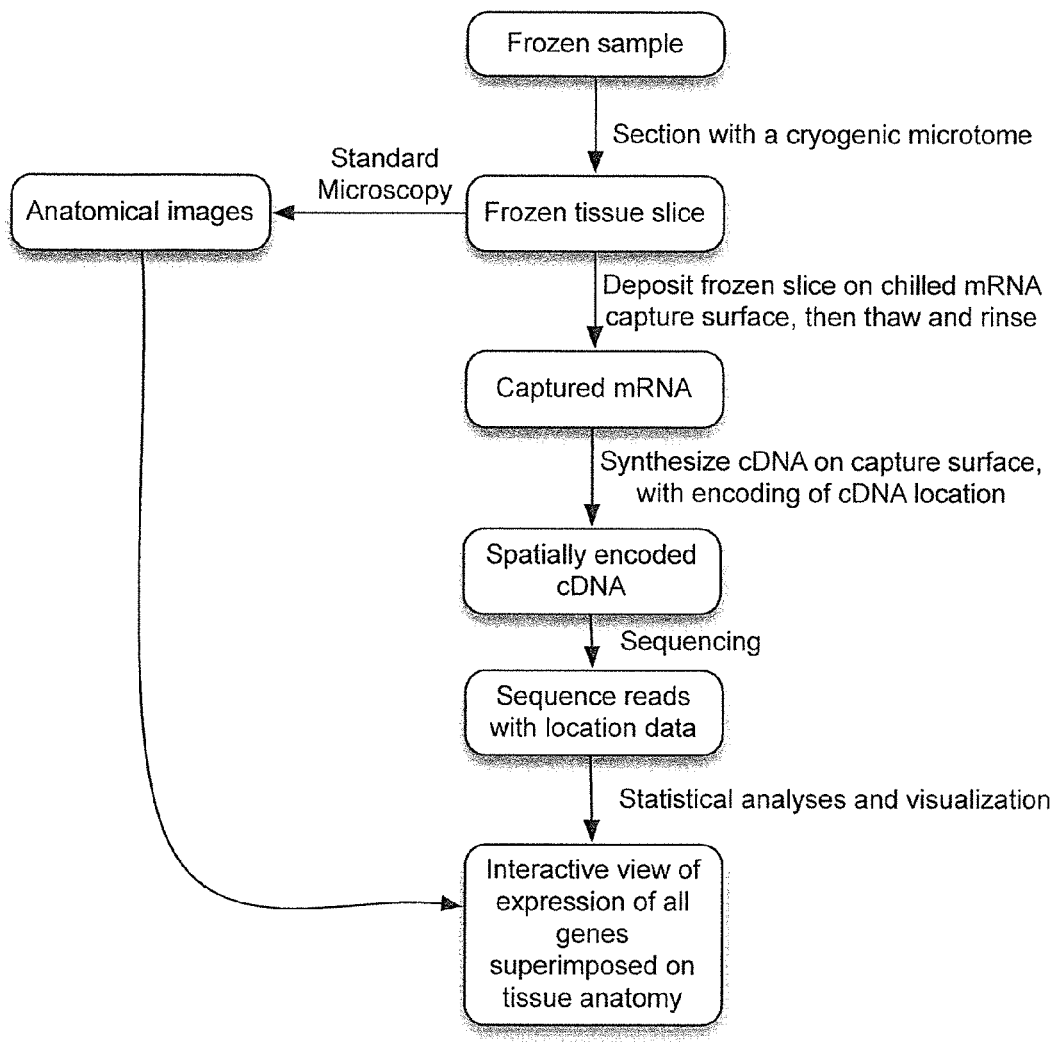
FIG. 1 is a process flow chart illustrating an embodiment of a gene expression camera system of the invention.
Figure 2:
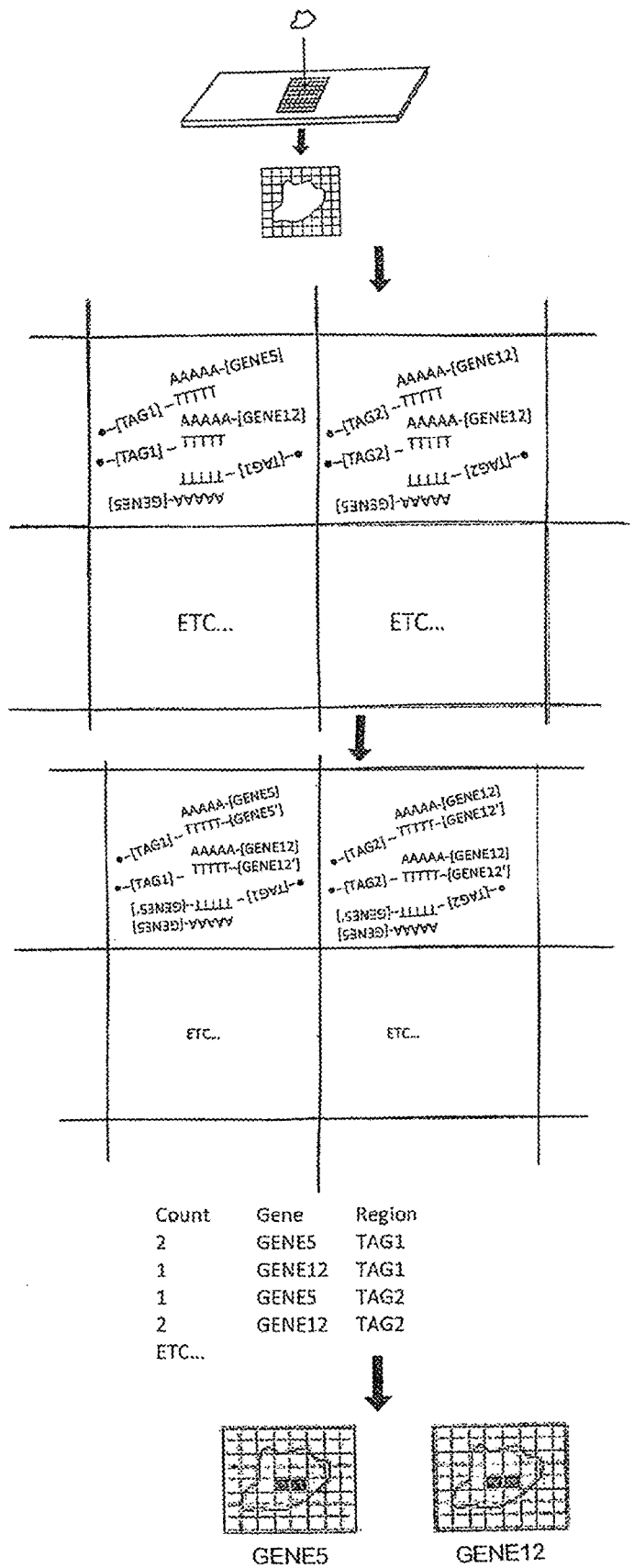
FIG. 2 is a drawing showing a frozen tissue slice (top) placed on a chilled substrate having a capture array. The capture array of bound capture adapters is shown enlarged to illustrate poly-T tails on each species of capture adapters capable of hybridizing to poly-A tails of mRNA species. Each capture adapter has a tag sequence that is specific to each region or address of the microarray (pixel). cDNA is synthesized as illustrated for two genes denoted gene5 and gene12, the cDNA copies indicated as gene5' and gene12'. Alternatively, the tag sequence is located on an adapter that is incorporated after capture. cDNA is liberated from the microarray and is sequenced and the number of sequences for each gene in each region is tabulated. The extent of the expression is monitored by the intensity of the signal.

Messenger RNA (mRNA) is a cell product or a product of in vitro RNA from a DNA template that constitutes large family of RNA molecules that convey genetic information from DNA to the ribosome (transcription), where the RNA molecules direct the specific amino acid sequence of the protein products of gene expression. Following transcription of primary transcript mRNA (pre-mRNA) by RNA polymerase, processed mature mRNA is translated into a polymer of amino acids, resulting in a protein. mRNA conveys the nucleotide sequence of a gene from the DNA in the genome (or in an organelle such as mitochondria) to the protein synthesis machinery. Expression of a gene results first in mRNA, and mRNA expression is an important and widely used measure of activity of a gene. Gene expression varies across tissues, cells, age, between species, disease states, and environmental conditions. Gene expression provides information regarding many other upstream and downstream biological activities.

Gene expression is measured by a number of tools such as microarrays, mRNA-sequencing, qPCR, in situ mRNA Hybridization, etc. The gene expression tools are used to measure the amount of expression of one or more genes at various times and subcellular, tissue or anatomic locations in an organism.

Gene expression tools that can measure a plurality of genes require the user to pre-dissect the tissue into a small number of regions (e.g. inner tumor and outer tumor). Tools with high spatial resolution only can measure a few pre-selected genes at a time and do not provide quantitative information. For many diagnostic and research applications broad spectrum analysis data from a plurality of genes at high spatial resolution with a high number of sequence identifications would be an important tool.

In present methodology it is standard to combine, gene expression tools (e.g., mRNA-sequencing followed by in situ mRNA hybridization) to obtain data from a plurality of genes at high spatial resolution. Combining gene expression tools is labor intensive and therefore expensive and the results are compromised. A newer fluorescent in situ RNA sequencing (FISSEQ) method sequences biomolecules directly within tissue, providing high spatial resolution of the expression of many genes. See Lee et al., Science DOI: 10.1126/science.1250212. The overall number of sequences, and hence statistical power, is relatively low compared to standard RNA sequencing approaches. Ibid.

Using a gene expression camera and spatial sequencing, by the methods of embodiments of the invention described herein, genes that are expressed are identified by the location of the binding of each gene to a detector and the spatial locations of the gene expression are obtained. The term "detector" as used herein refers to a device that detects by capturing or tracks and identifies biomolecules particularly nucleic acids for example DNA and RNA. The term "biomolecule" as used herein refers to a molecule that is produced by a living organism. The term biomolecule includes macromolecules such as proteins, polysaccharides, lipids, and nucleic acids, and small molecules such as primary metabolites, secondary metabolites, and natural products. The term "imagewise mapping" as used herein refers to a technique in which the feature of interest such as cellular or subcellular nucleic acids in the image are mapped with a set of locations located within the image.

The spatial location and the gene expression is specific to both cells and tissues. An embodiment of the invention uses these methods to complement histopathological classification of tumors.

The term "biosample" as used herein refers to a biological sample fluid that contains cells or to a tissue specimen. Biological fluids include lymph, blood, serum, urine, semen, mucus, saliva, tears, amniotic fluid, breast milk and perspiration, and include cell suspensions and solutions, cell lysates, intracellular fluids, extracellular fluids, interstitial fluids, etc. The tissue sample includes biopsy samples, autopsy samples, excised tissue and tumor samples including archived specimens and both fresh and preserved specimens. The term "micrograph" as used herein refers to a photograph or digital image taken through a microscope or similar device to show a magnified image of a feature not visible to the naked eye.

The following procedure outline describes an implementation of the invention as a gene expression camera, a sample preparation device, and use to image gene expression in a biosample.

Example 1

Construction of the Gene Expression Camera

The molecules for the detector element of the gene expression camera are produced using an array of synthetic oligonucleotides bound to a glass substrate. Each dot on the array is a mix of two oligonucleotides, a capture oligonucleotide and an indexing oligonucleotide. The capture nucleotide is the same for each dot, and each dot has an indexing oligonucleotide with a unique known sequence.

The capture DNA oligonucleotide has the general structure of order of nucleotide sequence 5'-[Linker]-[Spacer]-U-[3' primer]-[poly-T]-3', in which the linker is a modification group, such as an amine, that is used to bind the oligonucleotide to the array substrate. The spacer is a short sequence intended to reduce steric hindrance. The 3' primer nucleotide sequence creates a template for PCR amplification. The poly-T binds the mRNA.

The indexing oligonucleotide has the general structure of order of nucleotide sequence 5'-[Linker]-[Spacer]-U-[Sequencing primer]-[Index]-GGG-3'. The linker and spacer are as described herein. The sequencing primer is a sequence appropriate for PCR amplification and for creating a template for the forward sequencing primer of the sequencing platform to be used (for example, the Illumina Rd1SP primer). The index is an oligonucleotide sequence unique to the region (pixel). Each indexing oligonucleotide is mixed with capture oligonucleotide in spotting buffer and deposited onto the substrate in a known array position. This detector array is capable of being scaled up to be manufactured in bulk, and would be appropriate for use with any eukaryotic organism.

Example 2 mRNA Capture Using the Gene Expression Camera

The target tissue is cryosectioned, and one or more slices are set aside for use with the gene expression camera. Adjacent slices are imaged with standard microscopy methods to provide corresponding anatomical data. The gene camera patterned microarray is prechilled, and the cryoslice(s) deposited on the patterned microarray. The entire assembly is warmed, allowing the tissue to melt (thaw) and mRNA to bind by complementary hydrogen bonding to the capture oligonucleotides. Tissue debris is washed away with a wash buffer that contains poly-A oligonucleotides that bind to any remaining free capture oligonucleotides to reduce non-specific binding of mRNA.

Example 3 cDNA Synthesis Using the Gene Expression Camera

Reverse transcription mix (buffer, nucleotides, and a reverse transcriptase with template switching activity) is flowed onto the microarray and the complex is incubated at the appropriate temperature. Appropriate temperatures are calculated using standard methods such as Primer Blast. This results in first strand cDNA synthesis, templating on the captured mRNA and extending the primer of the capture oligonucleotide. The template switching activity of the reverse transcriptase results in the reverse complement of the indexing oligonucleotide being incorporated into the 3' end of the first strand cDNA. When first-strand cDNA synthesis is complete, Uracil-Specific Excision Reagent (e.g., USER Enzyme from New England Biolabs) is added to cleave the first strand cDNA and oligonucleotides from the microarray for further preparation in tubes.

Example 4

Library Preparation and Sequencing

First strand cDNA is amplified by Polymerase Chain Reaction (PCR) with two primers. The first corresponds to the 3' primer in the capture oligonucleotide. The second primer has a nucleotide sequence with the amplification and sequencing primer of the sequencing platform to be used (e.g., Illumina P5-Rd1SP) and is biotinylated at the 5' end. The PCR product is fragmented (e.g. by sonication with a Covaris shearing system), and the biotinylated fragments (which have the amplification and sequencing primer sequences, index, and sequence of the 5' end of the mRNA) are captured and purified on streptavidin coated beads. These are then end-repaired and A-tailed, and pre-annealed adapters are ligated to the fragments. These adapters contain the sequencing and amplification primer nucleotide sequences of the reverse read of the sequencing platform to be used. The library is then amplified by PCR, with the forward and reverse amplification primers specific to the sequencing platform. This library is sequenced according to standard single-end protocols with the forward sequencing adapter. The resulting single-end sequence reads include the index from the indexing oligonucleotide and a gene-specific tag from the mRNA. The index encodes the location at which the mRNA was captured, and the tag is mapped to a set of gene reference sequences to identify the gene.

Other embodiments of the invention employ a detector array in which the site-encoding nucleotide is incorporated in the capture nucleotide, in which case the captured material may be processed without requiring a template switching step.

Systems and articles of the invention, gene expression camera, are useful for biological investigation and diagnostic procedures to accelerate many existing investigative procedures by replacing multiple analyses or analysis steps with a single, quick high-throughput tool. Characterizing the spatial distribution of gene expression is essential to many research projects, as the distribution yielding data regarding where and when genes are active, and as such, immediately provides clues to the biological processes. These include, for example, metabolic, developmental or disease processes that are spatially heterogeneous. This detector reveals their spatial range or extent of their influence and their associated interdependencies. A developmental biologist could, for example, examine the distribution of gene expression in embryonic tissue slices to identify all genes that are uniquely expressed in a particular embryonic region. Spatial analyses of gene expression also have important diagnostic applications. Gene expression, for example, complements histopathological tumor classification and has the potential to greatly improve descriptions of heterogeneity within tumors or temporal progression of tumor traits.

Figure 3:
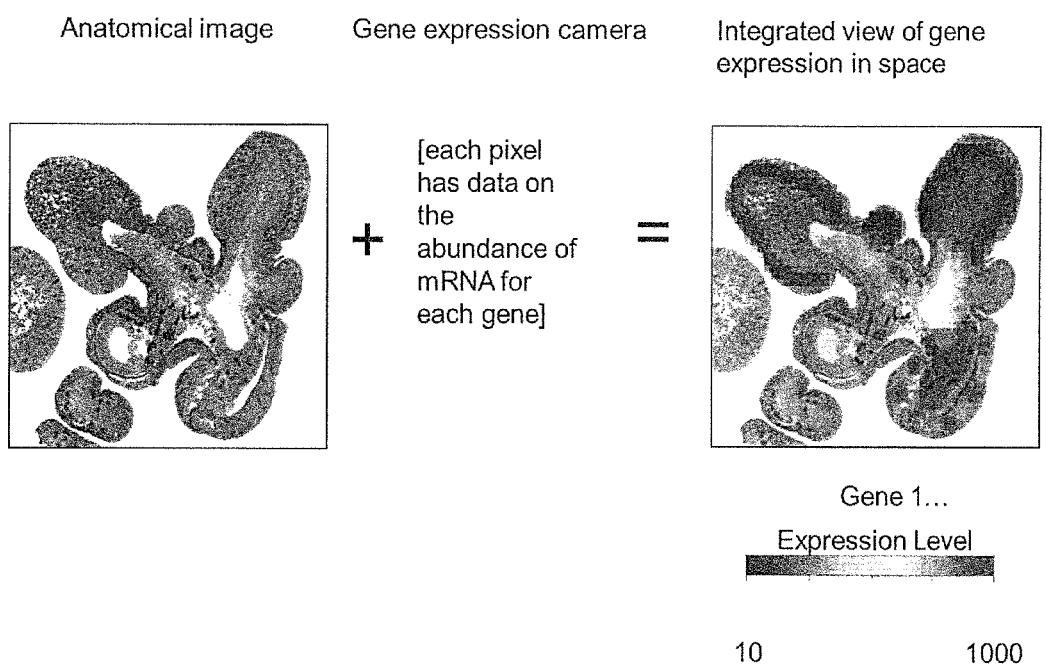
FIG. 3 is shows an anatomical image (left) and an integrated (right) gene expression image superimposed on the anatomical image. The gene expression camera measures the expression of a plurality of genes at high resolution in a two dimensional tissue slice, and the data is superimposed on the anatomical image of the same tissue slice. A plurality of gene expression data is simultaneously displayed using a plurality of colors.

Data obtained with the invention is displayed, or is viewed and analyzed in at least one of several standard methods. Displays include a heat map of normalized abundance for each gene or genome region, which is used by the investigator to flip through a deck of such images to look for nucleotide sequences with interesting patterns, or to pick out the image corresponding to the distribution of the abundance of a sequence of interest. Data is obtained from sample of a tissue as shown in FIG. 3. The intensity of the color corresponds to the gene expression. In an embodiment of the method, dimensional reduction of the data is performed, to identify sets of nucleotide sequences with spatially related patterns of abundance. Such images and data reductions allow investigators to ask and answer questions pertaining to: the most common expression patterns; identity of genes that have expression patterns similar to a gene of interest; identify genes that have expression patterns that are inversely related to the expression of a gene of interest; determine correspondence of expression of genes in a first sample to a second sample or to databases of known disease samples; to address the physico-chemical or histological properties of the source tissue. Gene expression quantification and sequencing data superimposed on microscopy images from adjacent tissue slices allow exploration of nucleotide sequence abundance in the context of tissue structure.

Capture detectors for the gene expression camera in another embodiment are prepared with pixel arrays of different pattern, spacing or extent to more effectively carry out specialized investigations. Thus, when intended to analyze or compare gene expression across the boundary of invasive and non-invasive tumors, an elongated band of capture-site-pixels is appropriate for displaying the changing distribution of gene expression along a single direction or axis; for mapping a colony or a sectioned mass, a concentric arrangement of pixels on circles of increasing radius proves useful. After initial determination of the amplitudes of expression and the relative efficiencies of the several steps necessary for sequencing, one can also construct arrays having pixels of different size to increase signal strength in one region (say the center or the edge of the specimen) or to increase spatial discrimination (resolution) in another region such as an edge or the neighborhood of a small structural feature such as a vascular or neural feature present in the specimen. Thus, specialized arrays are constructed for gross detection of expression in the sample, and for more localized characterization around fine features distributed in the sample. Other patterns, pixel sizes and pixel distributions are used to limit the amount of material sampled. Generally, it is contemplated that a detector may have as few as one or several pixels, or may be constructed with tens or hundreds of pixels.

Example 5

Spatially Resolved Genome Sequencing

In gene expression analyses as described in Example 1 or variations discussed above, mRNA is captured from the specimen, and sequenced directly or converted to cDNA for nucleotide sequencing. However, spatially-resolved genome sequencing, including targeted sequencing of particular genome regions, may also be accomplished by capturing genomic DNA rather than mRNA. Rather than a 'gene expression camera', this device or system or procedure constitutes a 'genome camera'; and is an alternative application of the spatially explicit or spatially resolved sequencing invention that enables the gene expression camera. This approach is, for example, advantageously applied to identify which regions of tumors have certain mutations.

Like the gene expression camera, a genome camera may be effected as a sample preparation device or as modified sequencing device. Genomic DNA rather than mRNA is captured on the detector. If the detector is a sample preparation device, a location-specific DNA sequence is added to the genome sequence and the thus-labeled molecules are liberated from the detector prior to sequencing. If the detector is a genome sequencing device, the location of the sequenced molecule on the detector or capture surface corresponds to its original position in the sample. The term "capture surface" as used herein refers to a surface, which is coated with binding materials that bind to specific biomolecules. For example, the capture surface is a slide coated with poly-T tails are capable of binding by Hydrogen bonding to the poly-A tails of mRNA. The capture surface is for example a slide, an array, a multiwell plate, a culture dish, etc. The capture surface includes at least one of a variety of materials such as glass, plastic or other polymers, stainless steel, metal, etc. Based on the application the capture surface is coated with at least one of a plurality of binding materials such as tags, primers, polypeptides, etc. Spatially explicit sequencing of DNA (whether whole genome or particular genomic regions isolated by targeted enrichment) thus permits analyses of the spatial distribution of mutations and structural genomic rearrangements within the tissue of an organism without requiring a priori knowledge of how a tissue would have to be dissected to identify such regions using conventional analysis or sequencing techniques. The invention makes it possible, for example, to identify which regions of a tumor have which mutations. It could also be applied to a metacommunity, such as an environmentally sampled biofilm, or the bacteria living on a mucosal surface, or the microbes at a wound site. The term "metacommunity" is used herein to refer to a set of interacting molecular communities, which are linked by the dispersal of multiple, potentially interacting species of biomolecules or extracellular macromolecules.

Spatially resolved genome sequencing of metacommunities would greatly improve our understanding of microbiomes by revealing which gene sequences are co-localized and by showing the spatial organization of different species and strains within the sample, not just their DNA sequences.

The invention being thus disclosed and several embodiments described, further embodiments and variations thereof will occur to those skilled in the art, and all such embodiments and variations are considered to be within the scope of the invention, as defined by the following claims and equivalents thereof.

What is claimed is:

1. A device or system for spatially resolved sequencing, comprising a detector having a capture surface adapted to capture biomolecules from a biosample for sequencing wherein both the sequence of a biomolecule and the location of the biomolecule within the original sample are recorded or displayed
    wherein the biospecimen is a tissue slice and the biomolecule sequence locations are mapped to an image of the slice to associate genes with anatomy of the imaged specimen,
    wherein the biomolecule is genomic DNA and the location and sequence of each DNA molecule is used to identify a spatially resolved image of different genotypes and
    wherein the biospecimen is a metacommunity such as an environmentally sampled bacterial film, a population of bacteria living on a mucosal surface, or the microbes at a wound site and the imagewise mapping of location reflects the location of different microbes.

2. The device or system of claim 1, wherein the biomolecule is messenger RNA (mRNA) and the location and sequence of each mRNA is used to generate a spatially resolved display of gene expression, thus forming a gene expression camera.

3. The device of claim 2, wherein the tissue slice is a tumor slice and the spatial array detects gene expression in regions, or in image-identifiable cells, of the tumor slice.

4. The device or system of claim 2, which is a modified sequencing flow cell wherein the biospecimen is contacted to and the mRNA is captured directly on a capture surface of the sequencing flow cell and is prepared for sequencing and then sequenced on the same surface.

5. A device or system for spatially resolved sequencing, comprising a detector having a capture surface adapted to capture biomolecules from a biosample for sequencing wherein both the sequence of a biomolecule and the location of the biomolecule within the original sample are recorded or displayed
    wherein the biospecimen is a tissue slice and the biomolecule sequence locations are mapped to an image of the slice to associate genes with anatomy of the imaged specimen
    wherein the biomolecule is messenger RNA (mRNA) and the location and sequence of each mRNA is used to generate a spatially resolved display of gene expression, thus forming a gene expression camera,
    wherein the captured mRNA is processed to incorporate a site-indexing oligonucleotide sequence forming an indexed sequence while bound to the detector, thereby forming a sample preparation device that incorporates site-indicating data in the sample, and wherein the detector is formed as an array of sites, each site bearing an mRNA capture oligonucleotide co-deposited with a site-encoding oligonucleotide, and the processing includes joining captured material to the site-encoding oligonucleotide at its site of capture, such that detection of the site-encoding oligonucleotide when sequencing identifies both the sequence and its position information for mapping distribution of gene expression in the biospecimen.

6. A method, article or system for imagewise mapping or display of genomic material or gene expression in a biosample, wherein the biosample is contacted to a detector to capture material therefrom at points of contact and the material is processed to identify capture position and sequence data so as to provide an imagewise display of genomic material or gene expression in the biosample wherein the method further comprises the steps of cryosectioning the biospecimen, forming a micrograph of a cryosectioned slice to display anatomical and/or structural elements of the biospecimen and contacting the cryosectioned slice or a second, adjacent slice to the detector so as to imagewise capture mRNA from the contacting slice on the detector for computational or imaging overlay of sequence data on the micrograph.

7. The method, article or system of claim 6, wherein the biosample is a tissue slice and the imagewise display is superimposed on an image of the tissue slice to correlate gene expression with structure of the tissue.

8. A method of mapping gene expression or occurrence of biomolecules in a region of a biospecimen, the method comprising the steps of
    (i) contacting the biospecimen to a detector having one or more capture sites adapted to capture DNA or mRNA from the sample;
    (ii) processing captured material, including amplifying and sequencing captured material, the detector being a capture surface of an automated flow sequencing system; and
    (iii) using associated capture site information to identify or display an image of the location of the biomolecules in the biospecimen,
    wherein the detector is formed as an array of sites, each site bearing an mRNA capture oligonucleotide co-deposited with a site-encoding oligonucleotide, and the processing includes joining captured material to the site-encoding oligonucleotide at its site of capture, such that detection of the site-encoding oligonucleotide when sequencing identifies both the sequence and its position information for mapping distribution of gene expression in the biospecimen.

9. The method of claim 8, wherein processing includes processing the captured material as it is held on the detector so that location of material on the detector provides said site-of-origin information for said material.

* * * * *